United States Patent
Adametz et al.

(10) Patent No.: US 10,653,853 B2
(45) Date of Patent: May 19, 2020

(54) APPARATUS FOR MONITORING A DISCONNECTION

(71) Applicant: Loewenstein Medical Technology S.A., Luxembourg (LU)

(72) Inventors: Benjamin Adametz, Hamburg (DE); Bjoern Tiemann, Hamburg (DE)

(73) Assignee: LOWENSTEIN MEDICAL TECHNOLOGY S.A., Luxembourg (LU)

( * ) Notice: Subject to any disclaimer, the term of this patent is extended or adjusted under 35 U.S.C. 154(b) by 751 days.

(21) Appl. No.: 15/287,265

(22) Filed: Oct. 6, 2016

(65) Prior Publication Data

US 2017/0100554 A1    Apr. 13, 2017

(30) Foreign Application Priority Data

Oct. 7, 2015  (DE) .................. 10 2015 012 930

(51) Int. Cl.
*A61M 16/00* (2006.01)
*A61M 39/10* (2006.01)

(52) U.S. Cl.
CPC ...... *A61M 16/0051* (2013.01); *A61M 16/026* (2017.08); *A61M 2016/003* (2013.01);
(Continued)

(58) Field of Classification Search
CPC ....... A61B 5/00; A61B 5/02028; A61B 5/021; A61B 5/022; A61B 5/0261; A61B 5/031; A61B 5/042; A61B 5/0422; A61B 5/0472; A61B 5/08; A61B 5/14553; A61B 5/1459; A61B 5/4064; A61B 5/6851; A61M 16/00; A61M 16/0003; A61M 16/0051; A61M 16/0063; A61M 16/0066; A61M 16/0069; A61M 16/024; A61M 16/026; A61M 16/06; A61M 16/0816; A61M 16/0833; A61M 16/101; A61M 16/1015; A61M 16/107; A61M 16/1075; A61M 16/16; A61M 16/202; A61M 16/204; A61M 16/205; A61M 16/206; A61M 16/208; A61M 2016/0021; A61M 2016/0027;
(Continued)

(56) References Cited

U.S. PATENT DOCUMENTS

| | | | | |
|---|---|---|---|---|
| 5,598,838 A | * | 2/1997 | Servidio | A61M 16/00 128/204.21 |
| 5,640,149 A | * | 6/1997 | Campbell | A61M 16/00 128/204.21 |

(Continued)

FOREIGN PATENT DOCUMENTS

| | | |
|---|---|---|
| EP | 968020 A1 | 1/2000 |
| WO | 9841268 A1 | 9/1998 |
| WO | 2014030098 A1 | 2/2014 |

*Primary Examiner* — Annette Dixon
(74) *Attorney, Agent, or Firm* — Abel Schillinger, LLP

(57) ABSTRACT

Disclosed are an apparatus and a method for monitoring the disconnection of a patient interface system during the ventilation, in which values which are indicative for the time curve of the respiratory gas flow are established and subjected to data evaluation, and wherein an alarm is triggered on the basis of the data evaluation if at least one value which is indicative for the time curve of the respiratory gas flow deviates from a specific limit value for a specific period of time.

17 Claims, 2 Drawing Sheets

(52) U.S. Cl.
CPC ............... *A61M 2016/0027* (2013.01); *A61M 2016/0039* (2013.01); *A61M 2016/0042* (2013.01); *A61M 2039/1005* (2013.01); *A61M 2205/14* (2013.01); *A61M 2205/15* (2013.01); *A61M 2205/18* (2013.01); *A61M 2205/3334* (2013.01); *A61M 2205/3365* (2013.01); *A61M 2205/505* (2013.01); *A61M 2205/52* (2013.01); *A61M 2230/432* (2013.01)

(58) Field of Classification Search
CPC .... A61M 2016/003; A61M 2016/0039; A61M 2016/0042; A61M 2016/1025; A61M 2202/0208; A61M 2205/13; A61M 2205/16; A61M 2205/17; A61M 2205/3303; A61M 2205/3334; A61M 2205/3365; A61M 2205/3368; A61M 2205/3375; A61M 2205/3553; A61M 2205/3561; A61M 2205/3569; A61M 2205/3584; A61M 2205/3592; A61M 2205/42; A61M 2205/50; A61M 2205/502; A61M 2205/505; A61M 2205/52; A61M 2205/581; A61M 2205/583; A61M 2205/8206; A61M 2205/8212; A61M 2230/205; A61M 2230/432; A61M 2230/435; A61N 1/056; A61N 1/37241; A61N 2001/0585; E05B 17/2057; E05B 61/00; E05B 65/00; H01L 21/28176; H01L 21/28202; H01L 21/28282; H01L 29/513; H01L 29/518; H01L 29/66833; H01L 29/792; H04L 12/40006; H04L 12/4625; H04L 2012/40273; H04L 63/08; Y10T 292/1033
See application file for complete search history.

(56) References Cited

U.S. PATENT DOCUMENTS

| | | | | |
|---|---|---|---|---|
| 5,664,562 | A * | 9/1997 | Bourdon | A61M 16/0069 128/204.18 |
| 5,881,717 | A | 3/1999 | Isaza | |
| 6,536,432 | B2 * | 3/2003 | Truschel | A61M 16/0051 128/202.22 |
| 9,283,339 | B2 * | 3/2016 | Sherman | A61M 16/024 |
| 2004/0016431 | A1 | 1/2004 | Preveyraud | |
| 2006/0086357 | A1 * | 4/2006 | Soliman | A61M 16/0051 128/204.22 |
| 2010/0071696 | A1 | 3/2010 | Jafari | |
| 2010/0078024 | A1 * | 4/2010 | Andrieux | A61M 16/0051 128/204.21 |
| 2013/0000644 | A1 * | 1/2013 | Thiessen | A61M 16/0051 128/204.23 |
| 2013/0239960 | A1 * | 9/2013 | Bertinetti | A61M 16/0066 128/202.22 |
| 2015/0144130 | A1 | 5/2015 | O'Donnell et al. | |
| 2015/0182710 | A1 * | 7/2015 | Berry Ann | A61M 16/0066 128/204.21 |

* cited by examiner

APPARATUS FOR MONITORING A DISCONNECTION

CROSS-REFERENCE TO RELATED APPLICATIONS

The present application claims priority under 35 U.S.C. § 119 of German Patent Application No. 10 2015 012 930.9, filed Oct. 7, 2015, the entire disclosure of which is expressly incorporated by reference herein.

BACKGROUND OF THE INVENTION

1. Field of the Invention

The present invention relates to the identification of faults in medical ventilation systems and a corresponding raising of an alarm in case of faults.

2. Discussion of Background Information

During the ventilation, the medical ventilator and the respiratory system of the patient form a coupled-together pneumatic system. The medical ventilator and the respiratory system are pneumatically coupled by way of the patient interface system, which consists of at least the ventilation tube and the patient interface (e.g. endotracheal tube or mask).

The disconnection (interruption of the connection) in the patient interface system is an unwanted state in which there is partial or complete pneumatic decoupling of parts of the patient interface system, consisting of e.g. the medical ventilator, the ventilation tube and a ventilation mask. As a consequence of the disconnection, the patient is no longer ventilated or no longer ventilated to an adequate extent. It is therefore necessary for the medical practitioner to identify a disconnection. A detection of and raising of an alarm in relation to a disconnection are part of the prior art.

The detection can be carried out by way of a pressure or flow measurement. In the case of a pressure measurement only carried out in the vicinity of the ventilator or in the case of using additional components such as a filter or a connection tube ("catheter mount") between exhale system and patient, this identification of a disconnection cannot be carried out by way of the pressure signal through the ventilator. When using the flow signal for detection, the detection threshold in the respiratory flow may be very different, depending on the connected components. In the case of a fixed detection threshold, there are false alarms or there is a lack of dependability.

However, it is not possible to set the alarm thresholds sensitively enough in the known ventilators, for example in order to trigger an alarm in good time where possible, as this would further increase the already unsatisfactorily high false alarm rate.

In view of the foregoing, it would be advantageous to have available an apparatus for monitoring a disconnection, which triggers an alarm in good time and reliably, while having a very low false alarm rate.

SUMMARY OF THE INVENTION

The present invention provides an apparatus which comprises a device for establishing values which are indicative for the time curve of the respiratory gas flow, the output signals of which are fed to a device for data evaluation, which in turn controls an alarm transmitter. The data evaluation device triggers an alarm on the alarm transmitter if at least one value which is indicative for the time curve of the respiratory gas flow deviates from a specific limit value for a specific period of time. In this way, it is possible to distinguish between a disconnection and a ventilation curve.

Advantageously, the apparatus may comprise a flow sensor and/or a pressure sensor. Alternatively, the apparatus may establish the flow and/or pressure from the rotational speed and/or power uptake of the ventilation fan.

The apparatus may comprise a $CO_2$ sensor in a complementary or alternative manner. By way of example, this $CO_2$ sensor detects the end tidal carbon dioxide ($etCO_2$) or the $CO_2$ content by way of a transcutaneous measurement.

In a complementary or alternative manner, a $CO_2$ sensor may be coupleable to the apparatus. By way of example, this $CO_2$ sensor detects the end tidal carbon dioxide ($etCO_2$) or the $CO_2$ content by way of a transcutaneous measurement.

An adaptive adaptation of the alarm is possible if the period of time and/or the limit value is/are adjustable.

The period of time and/or the limit value can also be stored in the ventilator or established continuously.

Advantageously, the limit value may be established under application of the movement equation, or equations derived therefrom, and taking into account values which are indicative for the time curve of the respiratory gas flow. In this way, it is possible to distinguish between a disconnection and a ventilation curve.

According to the invention, provision may also be made for the period of time and/or limit value to be adjusted automatically, for example on the basis of data from the patient interface system, and/or by the user via a user interface. The user interface may be a touchscreen or a display which depicts a selection field which is actuatable by way of an encoder.

Advantageously, the limit value may be the compliance (C) and/or the pressure (p) and/or the resistance (R) and/or the volume (V) and/or flow (V').

Advantageously, provision may moreover be made of an output unit for displaying the measurement values. By way of example, the output unit can be embodied as a touchscreen display.

A display and evaluation of the trigger may be provided in a complementary or alternative manner.

The present invention also provides a method for monitoring the disconnection of a patient interface system during the ventilation, in which values which are indicative for the time curve of the respiratory gas flow are established and subjected to data evaluation. An alarm is triggered on the basis of the data evaluation if at least one value which is indicative for the time curve of the respiratory gas flow deviates from a specific limit value for a specific period of time. In this way, it is possible to distinguish between a disconnection and a ventilation curve.

The method is preferably also characterized in that the period of time and/or the limit value is/are adjustable.

The method is preferably also characterized in that the period of time and/or the limit value is/are also stored in the ventilator or established continuously.

Advantageously, the limit value may be established under application of the movement equation, or equations derived therefrom, and taking into account values which are indicative for the time curve of the respiratory gas flow. In this way, it is possible to distinguish between a disconnection and a ventilation curve.

The method is preferably also characterized in that the period of time and/or limit value is/are adjusted automatically, for example on the basis of data from the patient interface system, and/or by the user via a user interface.

In the method according to the invention, provision may also be made for at least one measurement value to be displayed and at least one limit value for at least one measurement value of the respiratory gas flow and a time duration for the limit value to be predeterminable by way of the user interface.

The present invention also provides a controller which has elements for implementing the method set forth above.

According to the invention, provision may be made, in an alternative or complementary manner, for the respiratory gas to flow away freely from the ventilator with the patient interface system connected thereto, i.e. without a patient, and for the ventilator to store the pressure and/or flow values established in the process and take these into account as limit values for establishing a disconnection.

The user may predetermine a percentage value or a fraction of this flow-away value as a limit value.

Provision may also be made for the ventilator to automatically store and apply a percentage value or a fraction of this flow-away value as limit value.

According to the invention, provision may be be made of a flow sensor and a pressure sensor, the measurement values of which are both taken into account for establishing a disconnection. As a result of this measurement value redundancy, the reliability of the apparatus according to the invention is increased. As a result of this redundancy, the false alarm ratio can also be reduced further.

Advantageously, the data evaluation device triggers an alarm only if both established values lie below a specific limit value for a certain amount of time.

Since brief, one-time drops in pressure or flow in a time interval of up to 2 seconds do not constitute any danger, the adjustable limit value in the apparatus according to the invention is preferably e.g. from about 75% to about 85% of the established value. The alarm is triggered if the drop below this limit value exceeds a critical time interval which, advantageously, may be e.g. from about 3 to about 30 seconds, preferably from about 5 to about 10 seconds.

All values required for the individual case are advantageously buffer stored continuously in a rolling memory with e.g. a length of at least about 30 minutes. In the case of an alarm, the data of the last 30 minutes is transferred into a non-volatile memory, for example a hard disk drive, a memory card or the like. The data following the alarm is still written into the non-volatile memory for a certain further amount of time (e.g. for approximately 5 minutes) so that the medical practitioner has the time intervals before and after the alarm available for diagnosis.

Advantageously, the apparatus according to the invention also has a display, on which the measured values are displayed. In order to prevent relatively large jumps, the values are e.g. averaged over 2 seconds and only then displayed. In any case, an alarm is indicated acoustically and preferably also displayed optically. Moreover, secondary alarm notifications may be provided, which are e.g. triggered if the measurement values differ by more than an adjustable tolerance value (e.g. by more than about 3%) or if the battery voltage is too low or else if a different system malfunction occurs. It is essential here that the secondary system alarms differ clearly from an alarm.

Advantageously, the patient interface may be selected in a selection menu of the display. Depending on the selected patient interface, there are variations in the limit values for triggering the disconnection alarm.

By way of example, the disconnection alarm offers the possibility for individual fine adjustment. This is carried out by the user, for example in a selection menu of the display as admissible disconnection in percent (%). Here, 1% is the lowest limit value and 99% is the highest limit value. Preferably, it is possible to set values in the range from 1% to 99%. For example, in graded steps of 2% or 5%.

Preferably, the disconnection alarm can be deactivated in e.g. the following configurations: if the user selects a mask as patient interface and uses a leakage tube system; if the user selects a mouthpiece as patient interface.

According to the invention, disconnections can be reliably identified, for example by setting the admissible disconnection and the alarm activation time.

Provision may also be made of pre-settings for the admissible disconnection and/or the alarm activation time, which propose or apply values for the admissible disconnection and/or the activation time in accordance with the patient interface and/or the tube type and/or in accordance with the therapy settings.

According to the invention, it is also possible to set the activation time. This is the period of time which is required to trigger the alarm after a disconnection was identified. The adjustable period of time varies depending on patient interface and patient. In the case of an adult, e.g. 2-70 seconds can be set for the mask or invasive access patient interface. In the case of an adult, 2-700 seconds can be set for the mouthpiece patient interface. In the case of a child, e.g. 2-35 seconds can be set for the mask or invasive access or mouthpiece patient interface.

The activation time setting is displayed on the display for the user. In the case of a touchscreen, the activation time can also be set on the display.

Advantageously, the apparatus according to the invention also has an interface, by means of which alarm data can be transferred, either directly or by way of a modem, to a local computer or to a non-central evaluation computer in a clinic or practice of a medical practitioner.

Knowledge about the time of an alarm is important to the medical practitioner. For example, in order to be able to determine whether risk accumulations occur at specific times and/or in conjunction with specific events. Co-utilization of a real-time clock and recording of the real time in conjunction with alarm events are therefore advantageous.

By way of example, the apparatus therefore logs the alarms and outputs them by way of the interface, or displays them on the display, upon user selection.

BRIEF DESCRIPTION OF THE DRAWINGS

Further advantages and features of the present invention result from the description of the exemplary embodiment, which is explained hereafter with reference to the appended Figures.

In the Figures.

DETAILED DESCRIPTION OF EXEMPLARY EMBODIMENT

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
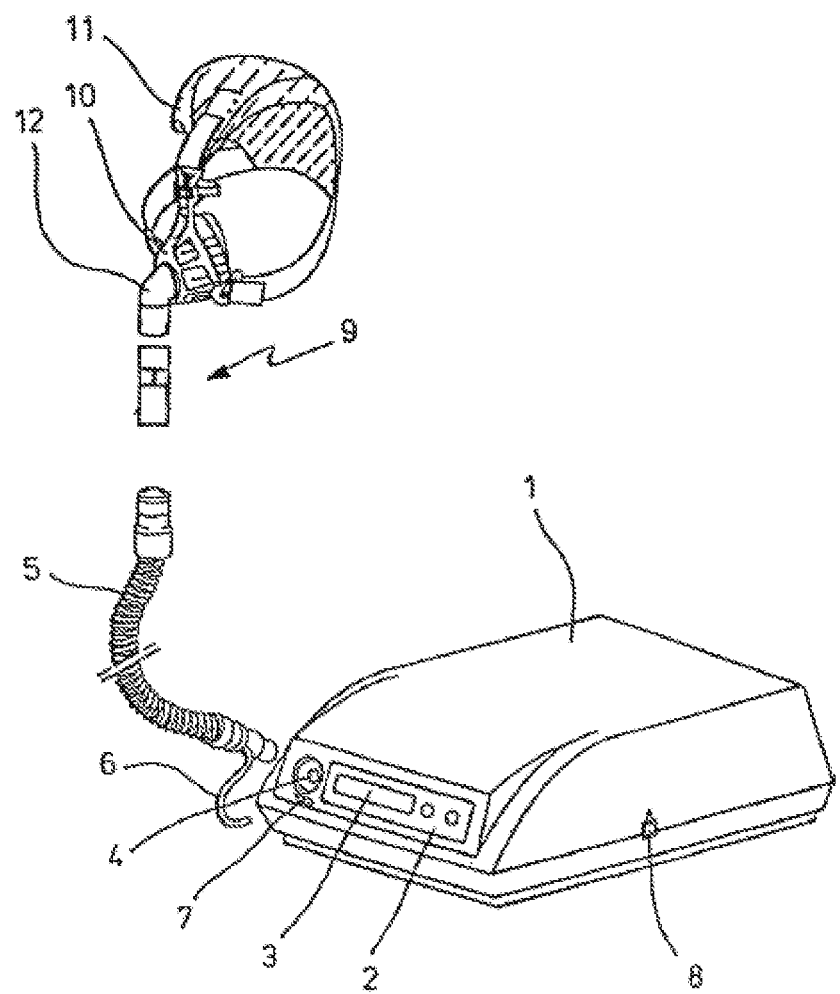
FIG. 1 shows the basic setup of an apparatus for ventilation.

FIG. 1 shows the basic setup of an apparatus for ventilation. Arranged in a ventilator interior in the region of the medical ventilator comprising a control field (2) and a display (3) is an electric motor (not displayed here) with a fan. A connection tube (5) is connected by way of a coupling (4). An additional pressure measuring tube (6) can extend along the connection tube (5), said pressure measuring tube being connectable to the ventilator housing (1) by way of a pressure input nozzle (7). In order to enable data transfer, the ventilator housing (1) has an interface (8). An expiration element/expiration valve (9) is arranged in the region of an extent of the connection tube (5) facing away from the ventilator housing (1).

FIG. 1 moreover shows a ventilation mask (10) which is embodied as a nasal mask. Affixment in the region of a head of a patient may be carried out by way of headgear (11). The ventilation mask/patient interface (10) has a coupling element (12) in the region of the extent thereof facing the connection tube (5).

The motor of the medical ventilator is realized as a multi-phase motor. Brushless and sensorless DC motors and synchronous motors may be used as a motor. A user interface for user information and/or user control is situated in the region of the ventilator housing. A respiratory gas pump is arranged in a ventilator interior, said respiratory gas pump being configured as an electric motor with a fan wheel, the operation of which is regulable by way of a motor controller. The operation of the motor and the power control thereof are regulable by the motor controller. The motor controller considers data from at least one sensor device. The sensor device establishes at least one signal related to the respiratory gas flow. By way of example, the sensor device may be embodied as a flow sensor and/or as a pressure sensor. An analyzer establishes inspiration phases and expiration phases from the signal related to the respiratory gas flow. The motor controller regulates the fan wheel rotational speed in a manner dependent on the established respiratory phase in such a way in at least one operating state that a substantially constant positive pressure is maintained during the inspiration phase. The motor is configured in such a way that a pressure range of e.g. 0 to 80 mbar can be set by changing the rotational speed. Pressure changes are realized by rotational speed changes of the fan wheel.

The apparatus for monitoring the disconnection of a patient interface system—which may consist of connection tube (5), expiration element/expiration valve (9), ventilation mask/patient interface (10), connection tube (5), coupling element (12), bacteria filter, humidifier, catheter mount—from a medical ventilator comprises a sensor device for establishing values of the respiratory gas flow, the output signals of which are fed to a device for data evaluation, which in turn controls an alarm transmitter, wherein the data evaluation device triggers an alarm on the alarm transmitter if at least one value of the respiratory gas flow deviates from a specific limit value for a specific period of time. The sensor device may comprise a flow sensor and/or a pressure sensor. By way of example, the period of time and/or the limit value is/are adjustable. The adjustment is carried out automatically, for example on the basis of data from the patient interface system and/or the adjustment is carried out by the user via a user interface. Moreover, provision is made of an output unit for displaying the measurement values.

Figure 2:
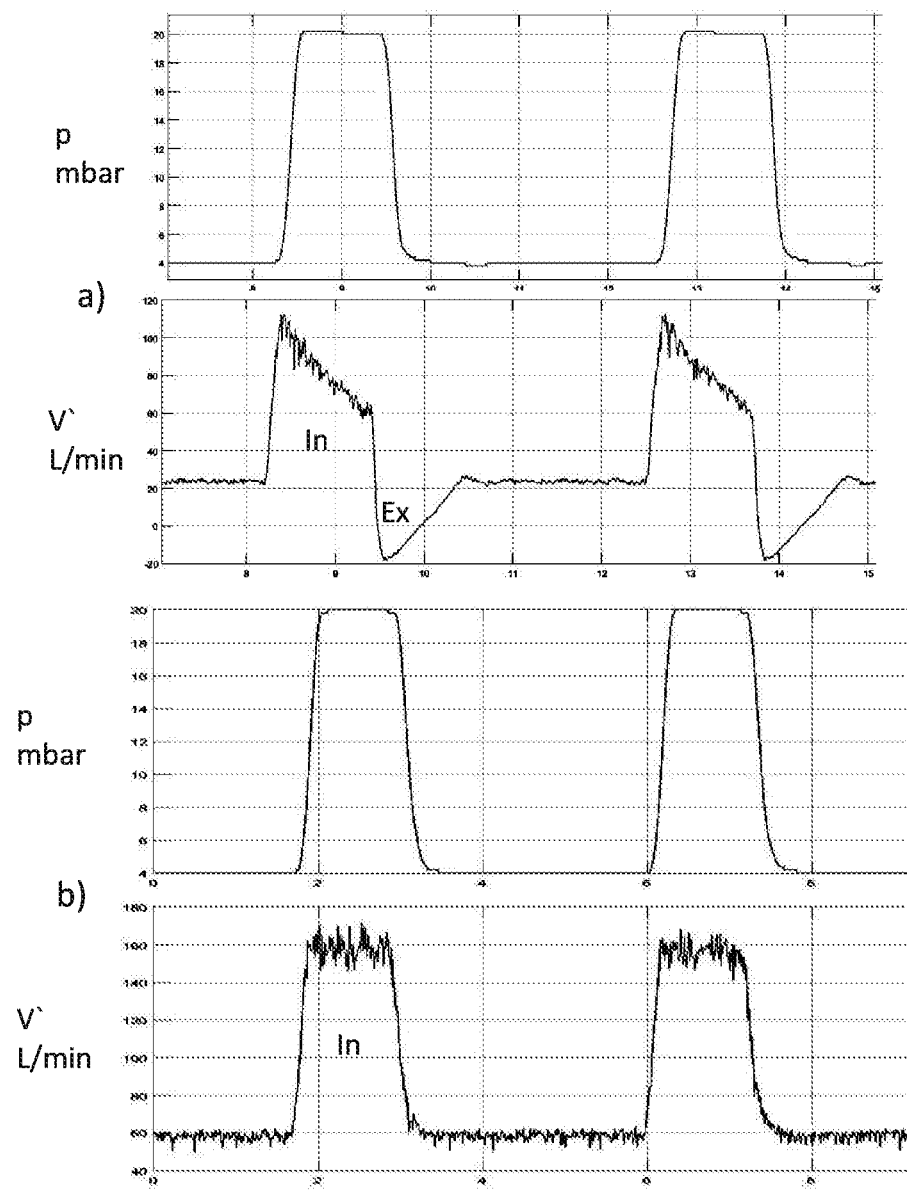
FIG. 2 shows pressure and flow curves during the ventilation.

FIG. 2 shows pressure and flow curves during the ventilation. At the top of subfigure a), it is possible to identify how a preset (inspiratory) pressure (p) for the ventilation sets in. The lower illustration shows the resulting flow (V'). The latter increases with the pressure stroke during inspiration (In) and falls below the initial level in the case of decreasing pressure during expiration (Ex). This is caused by the (negative) expiration flow.

It is recognized that the relationships between the pressure (p), compliance (C), volume (V), flow (V') and resistance (R) ventilation variables can be described by the movement equation:

$$\Delta P = (1/C)*V + R*V' \quad (80)$$

Subfigure b) of FIG. 2 depicts the situation from subfigure a) with a disconnection in the patient interface system. At the top, it is possible to identify how a preset (inspiratory) pressure (p) for the ventilation sets in. The lower illustration shows the resultant flow (V'). The latter increases with the pressure stroke during inspiration (In) and falls below the initial level in the case of decreasing pressure during expiration (Ex). However, the curve clearly differs from the flow curve from subfigure a). A substantial difference lies in the higher flow in the case of disconnection (approximately 160 l/min) compared to normal ventilation with approximately 115 l/min and in the missing expiration flow in the case of disconnection. The inspiratory flow and the expiratory flow may be modified in a characteristic manner, depending on where the disconnection is present and how much leakage flow is present in the region of the disconnection. This emerges mathematically from the movement equation; the compliance (C) becomes large in the case of a disconnection.

What is true as a matter of principle is that the dynamic respiratory mechanics can be established from the movement equation if a gas flow is present. By way of example, this opens up the possibility of simultaneously determining compliance and resistance. Alternatively, it is also possible to determine the flow curves to be expected in the case of a given or measured pressure. Hence, the presence of a disconnection can be deduced from the time curve if pressure and flow are measured.

To this end, various methods are conceivable:

The multiple linear regression analysis (Uhl R. R., Lewis F. J., Digital computer calculation of human pulmonary mechanics using a least squares fit technique. Comput Biomed Res. 1974 October; 7(5):48-95.) is a multi-point method and based on the linear RC model described by the movement equation.

The application of the multiple linear regression analysis presumes digital signal processing. A digital measurement system acquires the respiratory measurement data, airway pressure (Paw), respiratory gas volume (V) and respiratory gas flow (V') with a specific sampling frequency; i.e., the measurement system reads a Paw-V-V' value triple at defined times t1, t2, . . . tn. The movement equation is formulated for each value triple. Here, the following system of equations arises:

$$Paw(t1) = V(t1)/C + V'(t1)*R$$
$$Paw(t2) = V(t2)/C + V'(t2)*R$$
$$Paw(t3) = V(t3)/C + V'(t3)*R$$
$$...$$
$$Paw(tn) = V(tn)/C + V'(tn)*R$$

The sampling rate determines the number of measurement points acquired per breath and hence also the size of the system of equations from which the variables can be determined breath-by-breath.

In the slice method (Guttmann J., Eberhard L., Fabry B., et al., Determination of volume-dependent respiratory system mechanics in mechanically ventilated patients using the new SLICE method. Technol Health Care. 1994; 2:175-91), the multiple linear regression analysis is applied multiple times within a single breath. To this end, the breath volume is subdivided into 6 volume sections ("slices") of equal size. For each section, a value for compliance and resistance is determined in each case by means of multiple linear regression analysis (least squares fit). Hence, an intratidal curve of compliance and resistance may be determined for each breath.

Alternatively, the compliance can also be calculated in a computer-assisted manner by linear regression using the least squares method (least squares fit). Here, the movement equation is solved for all points of a breath and the combination of the influencing variables (R, C) by means of which the actual measurement values can be reproduced with the smallest square error is selected. This method is advantageous in that all data points of a breath are entered into the calculation and the possible error is minimized as a result thereof.

According to the invention, other methods which allow the presence of a disconnection to be deduced from at least the values for pressure and flow are also provided.

To this end, the apparatus for monitoring the disconnection of a patient interface system comprises a device for establishing values which are indicative for the time curve of the respiratory gas flow, the output signals of which are fed to a device for data evaluation (30), which in turn controls an alarm transmitter, wherein the data evaluation device triggers an alarm on the alarm transmitter if at least one value which is indicative for the time curve of the respiratory gas flow deviates from a specific limit value for a specific period of time. By way of example, the limit value emerges here from determining an idealized curve in comparison with the established, actual flow curve from the application of the movement equation. The limit value may be stored, or else it can be e.g. reestablished continuously. An example for a limit value is the compliance, which increases in the case of a disconnection. The pressure, which decreases in the case of a disconnection, may likewise be a limit value. It is possible to establish a value which is indicative for the time curve of the respiratory gas flow by applying the movement equation or equations derived therefrom. It is likewise possible to determine a limit value. A disconnection can be deduced from a change in the indicative value beyond the limit value.

The method for monitoring the disconnection of a patient interface system from a medical ventilator establishes, for example under application of the movement equation, values which are indicative for the time curve of the respiratory gas flow and subjects these to data evaluation, wherein an alarm is triggered on the basis of the data evaluation if at least one value which is indicative for the time curve of the respiratory gas flow deviates from a specific limit value for a specific period of time. In this case, the limit value emerges e.g. from determining an idealized curve in comparison with the established, actual flow curve from the application of the movement equation. In this way, it is possible to distinguish between a disconnection and a ventilation curve.

While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

LIST OF REFERENCE SIGNS

1 Ventilator housing
2 Control field
3 Display
4 Coupling
5 Connection tube
6 Pressure measuring tube
7 Pressure input nozzle
8 Interface
9 Expiration element/expiration valve
10 Ventilation mask/patient interface
11 Headgear
12 Coupling element

What is claimed is:

1. An apparatus for monitoring the disconnection of a patient interface system during ventilation, wherein the apparatus comprises a device for establishing values which are indicative for the time curve of a respiratory gas flow, output signals of which are fed to a data evaluation device, which in turn controls an alarm transmitter, the data evaluation device triggering an alarm on the alarm transmitter if at least one value which is indicative for a time curve of the respiratory gas flow deviates from a specific limit value for a specific period of time which depends on the patient interface and the patient, the limit value and/or the period of time being adjusted automatically.

2. The apparatus of claim 1, wherein the device for establishing values comprises a flow sensor and a pressure sensor.

3. The apparatus of claim 2, wherein a respiratory gas flows away freely from a ventilator with the patient interface system connected thereto, i.e., without a patient, and the ventilator stores pressure and flow values established in the process and takes these values into account as limit values for establishing a disconnection.

4. The apparatus of claim 3, wherein a percentage value or a fraction of a flow-away value may be predetermined as a limit value by a user.

5. The apparatus of claim 2, wherein the data evaluation device triggers an alarm only if established values for the flow sensor and the pressure sensor are both below a specific limit value for a specific period of time.

6. The apparatus of claim 1, wherein the period of time is adjustable.

7. The apparatus of claim 1, wherein the period of time and/or the limit value are stored in the ventilator or established continuously.

8. The apparatus of claim 6, wherein period of time and/or limit value values are adjusted on the basis of data from a patient interface system.

9. The apparatus of claim 1, wherein the limit value may be that of compliance and/or pressure and/or resistance and/or volume and/or flow.

10. The apparatus of claim 1, wherein the apparatus further comprises an output unit for displaying measurement values.

11. The apparatus of claim 1, wherein the period of time is from 3 seconds to 30 seconds.

12. The apparatus of claim 1, wherein the period of time is from 5 seconds to 10 seconds.

13. A method for monitoring the disconnection of a patient interface system during the ventilation, wherein the method comprises establishing and subjecting to data evaluation values which are indicative for a time curve of a respiratory gas flow, and wherein an alarm is triggered on the basis of the data evaluation if at least one value which is indicative for the time curve of the respiratory gas flow deviates from a specific limit value for a specific period of time which depends on the patient interface and the patient, the limit value and/or the period of time being adjusted automatically.

14. The method of claim 13, wherein the period of time and the limit value are adjustable.

15. The method of claim 13, wherein the period of time and/or the limit value are stored in the ventilator or established continuously.

16. The method of claim 13, wherein period of time and/or limit value values are adjusted on the basis of data from a patient interface system.

17. The method of claim 13, wherein at least one measurement value is displayed and at least one limit value for at least one measurement value of the respiratory gas flow and a time duration for the limit value are predeterminable by way of the user interface.

* * * * *